United States Patent [19]

Chen

[11] Patent Number: 5,433,227
[45] Date of Patent: Jul. 18, 1995

[54] HAND-HELD DENTAL FLOSS APPLICATOR APPARATUS

[76] Inventor: John C. Chen, 1115 W. Royal St. George Dr. Apt. 104, Naperville, Ill. 60563

[21] Appl. No.: 177,480
[22] Filed: Jan. 5, 1994
[51] Int. Cl.⁶ ............................................. A61C 15/00
[52] U.S. Cl. ..................................................... 132/323
[58] Field of Search ............... 132/321, 323, 324, 325, 132/326, 327; 242/405.1, 405.2; 248/175, 431, 435

[56] References Cited

U.S. PATENT DOCUMENTS

| | | | |
|---|---|---|---|
| 281,966 | 7/1883 | Burgess | 248/175 |
| 1,454,050 | 5/1923 | Gruenhagen | 242/405.1 |
| 1,570,357 | 1/1926 | Lawrence | 132/324 |
| 2,197,345 | 4/1940 | Meyer | 132/325 |
| 2,492,291 | 12/1949 | Johnson | 132/324 |
| 3,387,615 | 6/1968 | Macken | 132/323 |
| 3,830,246 | 8/1974 | Gillings | 132/321 |
| 3,897,796 | 8/1975 | Erickson | 132/321 |
| 3,930,059 | 12/1975 | Wells | 132/325 X |
| 4,002,183 | 1/1977 | Restall | 132/323 |
| 4,440,184 | 4/1984 | Smith | 132/323 |
| 4,570,653 | 2/1986 | Wolf | 132/91 |
| 4,655,233 | 4/1987 | Laughlin | 132/323 |
| 4,827,952 | 5/1989 | Kos | 132/323 |
| 4,875,649 | 10/1989 | Bendig, Jr. | 248/175 X |
| 4,966,176 | 10/1990 | Lachenberg | 132/325 |
| 5,064,150 | 11/1991 | Prouty | 242/405.1 X |
| 5,123,432 | 1/1992 | Wyss | 132/323 |
| 5,145,122 | 9/1992 | Poister | 242/405.1 X |
| 5,183,064 | 2/1993 | Barth | 132/323 |
| 5,184,632 | 2/1993 | Gross et al. | 132/326 |
| 5,232,002 | 8/1993 | McClallen | 132/323 X |

Primary Examiner—Nicholas D. Lucchesi

[57] ABSTRACT

A new and improved hand-held dental floss applicator apparatus includes a central body assembly, four finger assemblies projecting from the central body assembly, and four dental floss receiving assemblies connected to the respective four finger assemblies. Each of the respective dental floss receiving assemblies is formed as a notch in a respective finger assembly. The central body assembly lies in a first plane. A respective first portion of each of the respective finger assemblies projects from the central body assembly and is co-planar with the central body assembly. A respective second portion of each of the respective finger assemblies projects from each of the respective first portions and includes an end portion that lies in a second plane that is substantially perpendicular to the first plane. The central body assembly includes two opposed dental floss receiving channels. The dental floss receiving channels are formed as indentations adjacent to flange portions formed in the central body assembly. In accordance with another aspect of the invention, a combined hand-held dental floss applicator and dental floss apparatus is provided in which the dental floss receiving assemblies are adapted to receive respective beads of a beaded dental floss. The dental floss apparatus includes a beaded dental floss which includes beads spaced at predetermined intervals along a quantity of dental floss. The predetermined intervals are approximately equal to a transverse distance between opposite resilient finger assemblies on opposite sides of a centrally positioned longitudinal plane.

8 Claims, 4 Drawing Sheets

HAND-HELD DENTAL FLOSS APPLICATOR APPARATUS

BACKGROUND OF THE INVENTION

1. Field of the Invention

The present invention relates generally to dental floss and hand-held applicators for applying the dental floss to a person's teeth and gums.

2. Description of the Prior Art

The periodic application of dental floss to teeth and gums is generally considered to be both a prophylactic and therapeutic activity for promoting dental health. One way of applying dental floss is for a person to cut off a piece of dental floss, wrap each end of the cut off piece around a respective finger on different hands, and applying the floss to the teeth and gums as the floss is stretched between the respective fingers of the respective hands. A number of disadvantages are associated with this technique. A relatively large amount of dental floss must be used to wrap around the two fingers in addition to providing an amount of floss to be applied to the teeth and gums. In this respect, this method is quite wasteful of the dental floss. With this technique, to get the floss properly positioned next to the teeth and gums, it is necessary to place one finger in the mouth. Placing a finger in the mouth can be undesirable for a number of reasons. The finger may not be clean or sanitary. The appearance of a finger in a mouth may be deemed impolite and embarrassing. A large finger in a small mouth may be difficult to maneuver. When the finger is removed from the mouth, saliva will inevitably be present on the finger. In this respect, it would be desirable to apply dental floss without placing a finger in the mouth.

Throughout the years, a number of innovations have been developed relating to hand-held implements used for applying dental floss to teeth and gums, and the following U.S. patents are representative of some of those innovations: U.S. Pat. Nos. 4,570,653; 4,827,952; 4,966,176; 5,183,064; and 5,184,632. More specifically, U.S. Pat. No. 4,570,653 discloses a V-shaped device that is used in conjunction with dental floss to wipe sides of adjacent teeth.

U.S. Pat. No. 4,827,952 discloses a dental flosser that has extensible arms on live hinges. A beaded dental floss is used on the hinged arms. Moving hinge parts always have the disadvantage of the tendency for the moving parts to wear out. More specifically, after flexing numerous times, the living hinges are susceptible to material fatigue and breakage. In this respect, it would be desirable if a hand-held dental flosser were provided which did not include living hinges that are subject to material fatigue and breakage upon repeated use.

U.S. Pat. No. 4,966,176 discloses a hand-held dental flosser which includes a spool of floss and a section for keeping some of the floss taut. A disadvantage of having the floss spool intimately associated with the hand-held flosser is that the spool of floss is susceptible to contamination. In this respect, it would be desirable if a hand-held dental flosser were provided which does not include a spool of dental floss in the hand-held device.

U.S. Pat. No. 5,183,064 discloses a hand-held dental flosser which includes a guide rod attached to one end of a segment of dental floss and includes a button attached to the other end of the dental floss segment. Such a device appears to requires that the dental floss is supplied in specific segments having a guide rod attached at one end and a button attached at the other end of the dental floss. Such a device does not permit the use of conventional dental floss that is supplied as a continuous thread on a spool. In this respect, it would be desirable if a hand-held dental flosser were provided which can use conventional dental floss provided on a spool.

U.S. Pat. No. 5,184,632 discloses a battery-powered, motorized, handheld dental flosser. The risks of water and electricity are well known. In addition, the complexities of this device make is relatively bulky, heavy, and expensive. In this respect, it would be desirable if a hand-held dental flosser were provided which is simple in design and construction, is simple in operation, and is inexpensive.

Still other features would be desirable in a hand-held dental floss applicator apparatus. For example, the prior art dental flosser devices employ only one taut segment of dental floss that is suitable for applying to the teeth and gums. In this respect, it would be desirable if a hand-held dental flosser were provided which included two taut segments of dental floss that are suitable for applying to the teeth and gums. A hand-held dental flosser that has more than one dental flossing area is a more efficient dental flosser.

For a hand-held dental flosser that must be loaded with a segment of dental floss, it may be difficult to estimate the proper length of dental floss to be cut off of a spool for the hand-held flosser. In this respect, it would be desirable if a hand-held dental flosser were provided with dental floss that had color markings which indicate places at which the dental floss should be cut for loading; the hand-held dental flosser.

The use of beaded dental floss may have some advantages. In this respect, it would be deskable if a hand-held dental flosser were provided with a spool of beaded dental floss that had beads spaced apart predetermined distances to coincide with proper loading of the hand-held dental flosser.

Thus, while the foregoing body of prior art indicates it to be well known to use hand-held dental flossers, the prior art described above does not teach or suggest a hand-held dental floss applicator apparatus which has the following combination of desirable features: (1) is not wasteful of dental floss; (2) permits application of dental floss without placing a finger in the mouth; (3) does not include living hinges that are subject to plastic fatigue and breakage upon repeated use; (4) does not include a spool of dental floss carried in the hand-held device; (5) can use conventional dental floss provided on a spool; (6) is simple in design and construction, is simple in operation, and is inexpensive; (7) includes two taut segments of dental floss that are suitable for applying to the teeth and gums; (8) is provided with dental floss that has color markings which indicate places at which the dental floss should be cut off the spool to provide a dental floss segment for loading the hand-held dental flosser; and (9) is provided with a spool of beaded dental floss that has beads spaced apart at predetermined distances to coincide with proper loading of the hand-held dental flosser. The foregoing desired characteristics are provided by the unique hand-held dental floss applicator apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a new and improved hand-held dental floss applicator apparatus which includes a central body assembly, four finger assemblies projecting from the central body assembly, and four dental floss receiving assemblies connected to the respective four finger assemblies. Each of the respective dental floss receiving assemblies is formed as a notch in a respective finger assembly.

The central body assembly lies in a first plane. A respective first portion of each of the respective finger assemblies projects from the central body assembly and is co-planar with the central body assembly. A respective second portion of each of the respective finger assemblies projects from each of the respective first portions and includes an end portion that lies in a second plane that is substantially perpendicular to the first plane.

The central body assembly includes two opposed dental floss receiving channels. The dental floss receiving channels are formed as indentations adjacent to flange portions formed in the central body assembly. A centrally positioned longitudinal plane is perpendicular to the first plane and divides the central body assembly and the finger assemblies into two first bilaterally symmetrical portions. Each of the first symmetrical portions lies on one side of the centrally positioned longitudinal plane. A centrally positioned transverse plane is perpendicular to the first plane and divides the central body assembly and the finger assemblies into two second bilaterally symmetrical portions. Each of the second symmetrical portions lies on one side of the centrally positioned transverse plane.

In accordance with another aspect of the invention, a combined hand-held dental floss applicator and dental floss apparatus is provided. The hand-held dental floss applicator apparatus includes a central body assembly, four resilient finger assemblies projecting from the central body assembly, and four dental floss receiving assemblies connected to the respective four finger assemblies. Each of the respective dental floss receiving assemblies includes a bead-receiving portion that has a shape complementary to a bead that is received. The beads are on a segment of beaded dental floss.

The dental floss apparatus includes a beaded dental floss which includes beads spaced at predetermined intervals along a quantity of dental floss. The predetermined intervals are approximately equal to a transverse distance between opposite resilient finger assemblies on opposite sides of a centrally positioned longitudinal plane that divides the central body assembly and the finger assemblies into two first bilaterally symmetrical portions wherein each of the first symmetrical portions lies on one side of the centrally positioned longitudinal plane.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining at least two preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Pat. and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

It is therefore an object of the present invention to provide a new and improved hand-held dental floss applicator apparatus which has all of the advantages of the prior art and none of the disadvantages.

It is another object of the present invention to provide a new and improved hand-held dental floss applicator apparatus which may be easily and efficiently manufactured and marketed.

It is a further object of the present invention to provide a new and improved hand-held dental floss applicator apparatus which is of durable and reliable construction.

An even further object of the present invention is to provide a new and improved hand-held dental floss applicator apparatus which is susceptible of a low cost of manufacture with regard to both materials and labor, and which accordingly is then susceptible of low prices of sale to the consuming public, thereby making such hand-held dental floss applicator apparatus available to the buying public.

Still yet a further object of the present invention is to provide a new and improved hand-held dental floss applicator apparatus which is not wasteful of dental floss.

Still another object of the present invention is to provide a new and improved hand-held dental floss applicator apparatus that permits application of dental floss without placing a finger in the mouth.

Yet another object of the present invention is to provide a new and improved hand-held dental floss applicator apparatus which does not include living hinges that are subject to plastic fatigue and breakage upon repeated use.

Even another object of the present invention is to provide a new and improved hand-held dental floss applicator apparatus that does not include a spool of dental floss carried in the hand-held device.

Still a further object of the present invention is to provide a new and improved hand-held dental floss applicator apparatus which can use conventional dental floss provided on a spool.

Yet another object of the present invention is to provide a new and improved hand-held dental floss applicator apparatus that is simple in design and construction, is simple in operation, and is inexpensive.

Still another object of the present invention is to provide a new and improved hand-held dental floss applicator apparatus which includes two taut segments of dental floss that are suitable for applying to the teeth and gums.

Yet another object of the present invention is to provide a new and improved hand-held dental floss applicator apparatus that is provided with dental floss that has color markings which indicate places at which the dental floss should be cut off the spool to provide a dental floss segment for loading the hand-held dental flosser.

Still a further object of the present invention is to provide a new and improved hand-held dental floss applicator apparatus that is provided with a spool of beaded dental floss that has beads spaced apart at predetermined distances to coincide with proper loading of the hand-held dental flosser.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein.

DESCRIPTION OF THE PREFERRED EMBODIMENT

Figure 1:
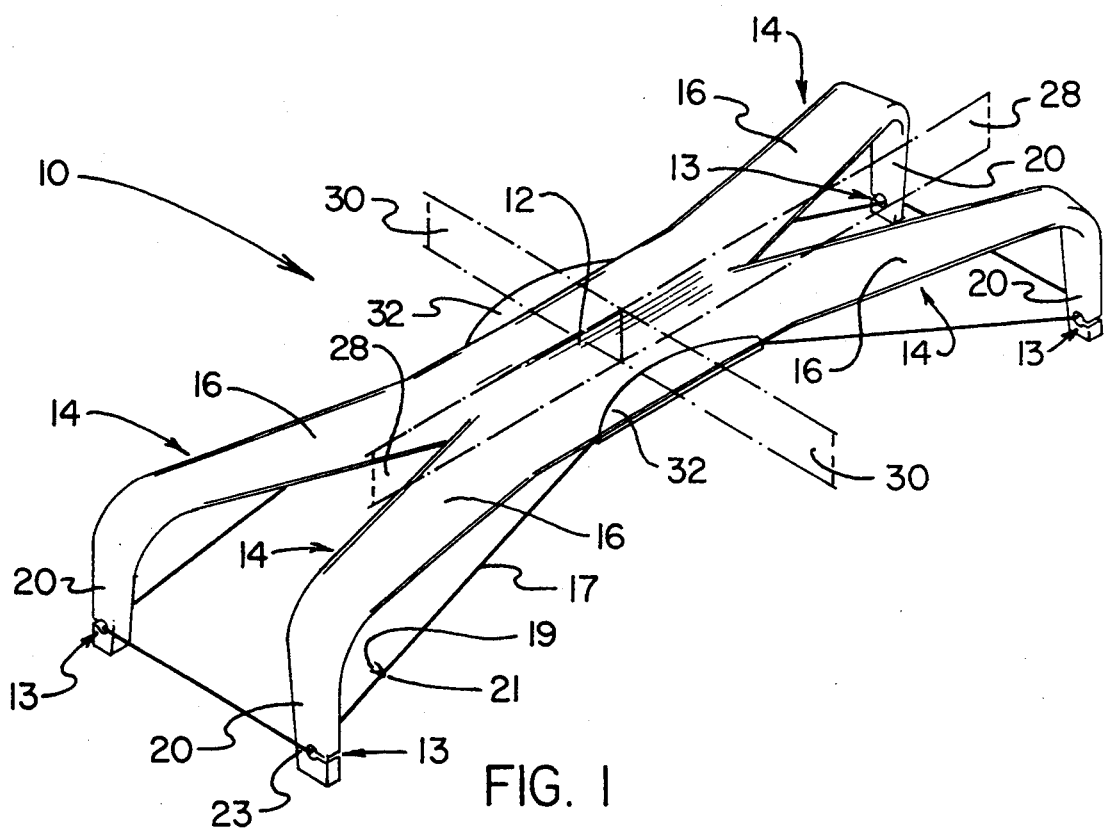
FIG. 1 is a perspective view showing a first preferred embodiment of the hand-held dental floss applicator apparatus of the invention which is used with conventional or color-coded dental floss on a spool.
Figure 2:
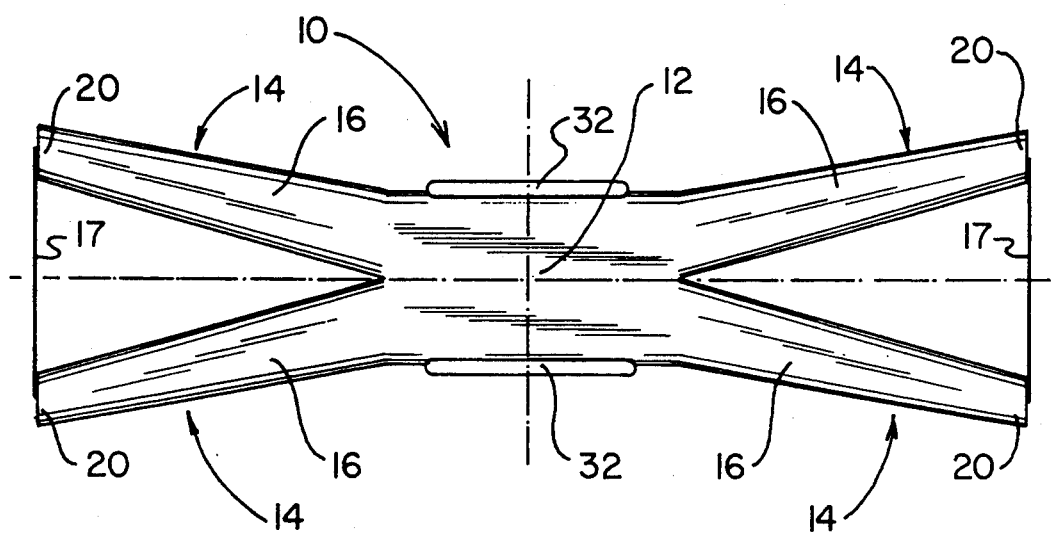
FIG. 2 is a top view of the embodiment of the hand-held dental floss applicator apparatus shown in FIG. 1.
Figure 3:
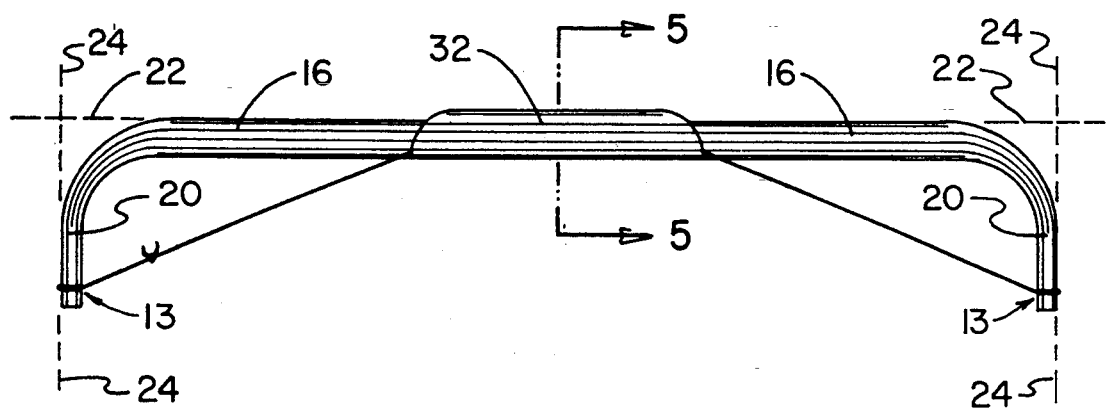
FIG. 3 is a side view of the embodiment of the invention shown in FIG. 2.
Figure 4:
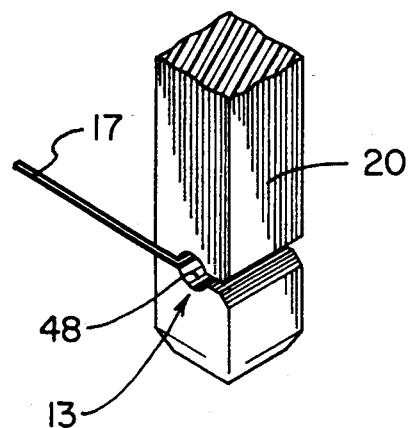
FIG. 4 is an enlarged perspective view of an end of a finger portion of the embodiment of the invention shown in FIG. 3.
Figure 5:
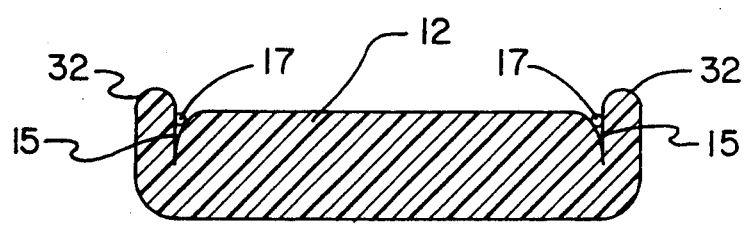
FIG. 5 is an enlarged partial cross-sectional view of the embodiment of the invention shown in FIG. 3 taken along line 5—5 of FIG. 3.

With reference to the drawings, a new and improved hand-held dental floss applicator apparatus embodying the principles and concepts of the present invention will be described.

Turning initially to FIGS. 1-5, there is shown a first exemplary embodiment of the hand-held dental floss applicator apparatus of the invention generally designated by reference numeral 10. In its preferred form, hand-held dental floss applicator apparatus 10 includes a central body assembly 12, four finger assemblies 14 projecting from the central body assembly 12, and four dental floss receiving assemblies 13 connected to the respective four finger assemblies 14.

The central body assembly 12 lies in a first plane 22. A respective first portion 16 of each of the respective finger assemblies 14 projects from the central body assembly 12 and is co-planar with the central body assembly 12. A respective second portion of each of the respective finger assemblies 14 projects from each of the respective first portions 16 and includes an end portion 20 that lies in a second plane 24 that is substantially perpendicular to the first plane 22. More specifically, each of the respective dental floss receiving assemblies 13 is formed as a notch 13 in a respective end portion 20 of the finger assembly 14.

The central body assembly 12 includes two opposed dental floss receiving channels 15. The dental floss receiving channels 15 are formed as indentations adjacent to flange portions 32 formed in the central body assembly 12. A centrally positioned longitudinal plane 28 is perpendicular to the first plane 22 and divides the central body assembly 12 and the finger assemblies 14 into two first bilaterally symmetrical portions. Each of the first symmetrical portions lies on one side of the centrally positioned longitudinal plane 28. A centrally positioned transverse plane 30 is perpendicular to the first plane 22 and divides the central body assembly 12 and the finger assemblies 14 into two second bilaterally symmetrical portions. Each of the second symmetrical portions lies on one side of the centrally positioned transverse plane 30. The configuration of the hand-held dental floss applicator apparatus 10 of the invention may be referred to as a Siamese bow dental flosser due to its resemblance to a Siamese bow.

In use, a length of conventional dental floss 17 is threaded through the respective notches 13 on the end portions 20 of the finger assemblies 14. The dental floss 17 is also threaded through the dental floss receiving channels 15 on the central body assembly 12. Two ends of the dental floss 17 are tied together to form a knot 19.

In accordance with another aspect of the invention, the dental floss is on a spool and is color coded. More specifically, a spot of a first color 21, e.g. red, is located on a segment of the dental floss to locate where the dental floss is to be cut so that it will fit properly on the hand-held dental floss applicator apparatus of the invention when the dental floss is threaded through the respective notches 13 and the dental floss receiving channels 15. In addition, the knot 19 is located on the spot of the first color 21. In addition, a spot of a second color 23, e.g. blue, is located at a position on the segment of dental floss 17 which is positioned at a specific notch 13 which serves as a benchmark or point of origin.

Stated somewhat differently, this aspect of the invention which includes color coded dental floss provides for the combination of the hand-held dental floss applicator apparatus 10 and the color coded dental floss.

Turning to FIGS. 6–9, a second embodiment of the invention is shown. Reference numerals are shown that correspond to like reference numerals that designate like elements shown in the other figures. In this embodiment, combined hand-held dental floss applicator and dental floss apparatus is provided. The hand-held dental floss applicator apparatus 10 includes a central body assembly 12, four resilient finger assemblies 14 projecting from the central body assembly 12, and four dental floss receiving assemblies 13 connected to the respective four finger assemblies 14. Each of the respective dental floss receiving assemblies 13 includes a bead-receiving portion 48 that has a shape complementary to a bead 38 that is received. The beads 38 are on a segment of beaded dental floss 36.

The dental floss apparatus includes a beaded dental floss 36 which includes beads 38 spaced at predetermined intervals along a quantity of dental floss. The predetermined intervals are approximately equal to a transverse distance 40 between opposite resilient finger assemblies 14 on opposite sides of a centrally positioned longitudinal plane 28 that divides the central body assembly 12 and the finger assemblies 14 into two first bilaterally symmetrical portions wherein each of the first symmetrical portions lies on one side of the centrally positioned longitudinal plane 28.

Figure 6:
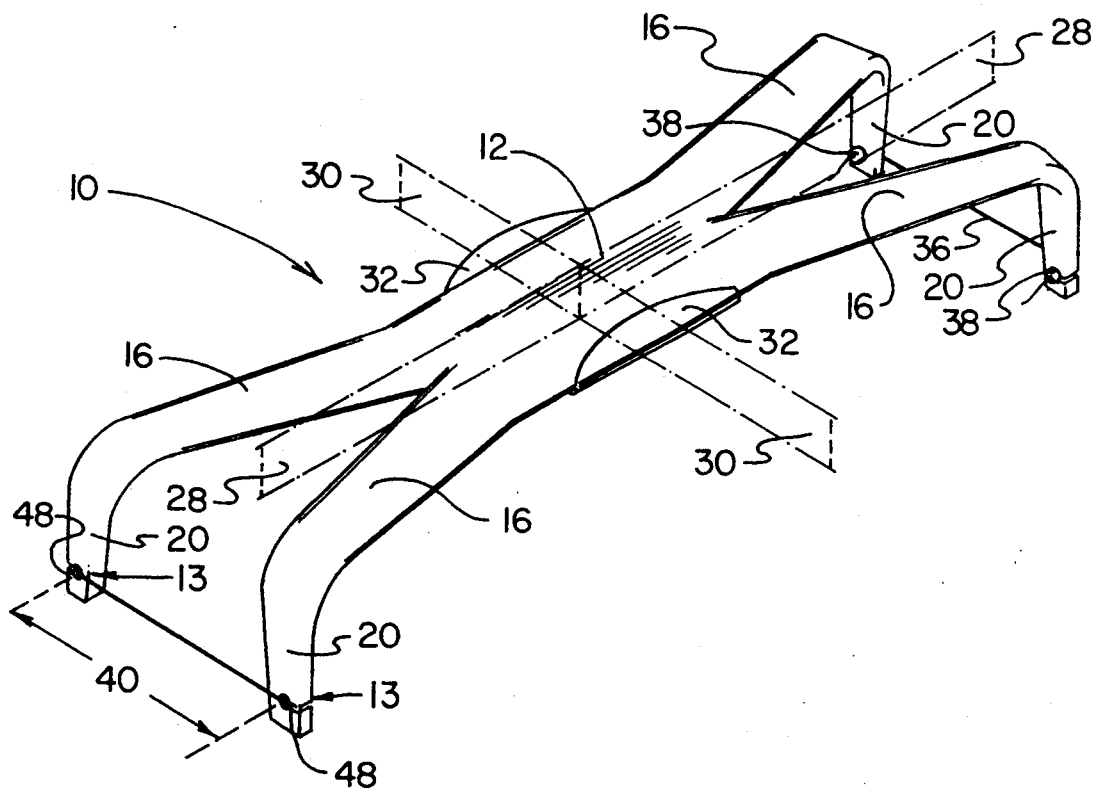
FIG. 6 is a perspective view showing a second preferred embodiment of the hand-held dental floss applicator apparatus of the invention which is used with beaded dental floss on a spool.
Figure 7:
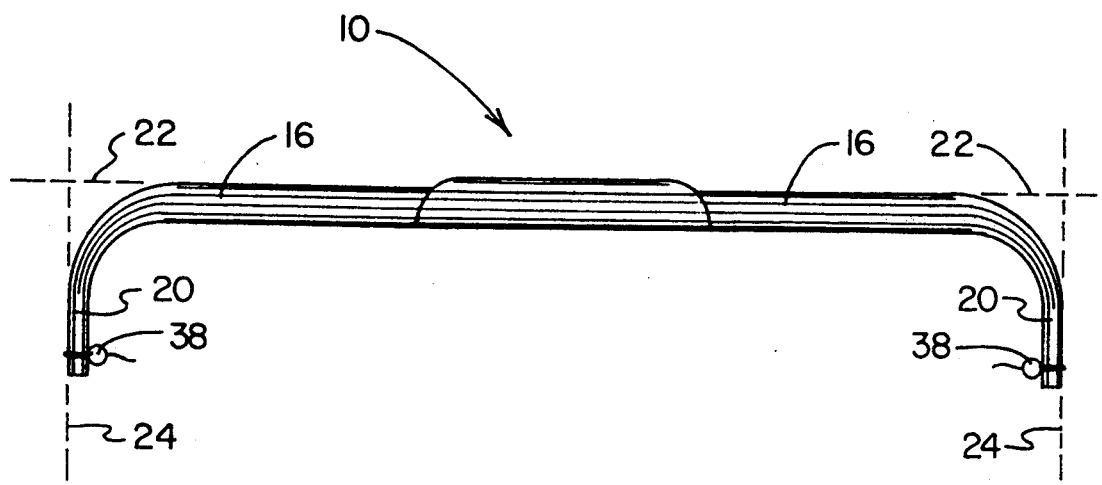
FIG. 7 is a side view of the embodiment of the hand-held dental floss applicator apparatus shown in FIG. 6 showing two pieces of beaded dental floss installed.
Figure 8:
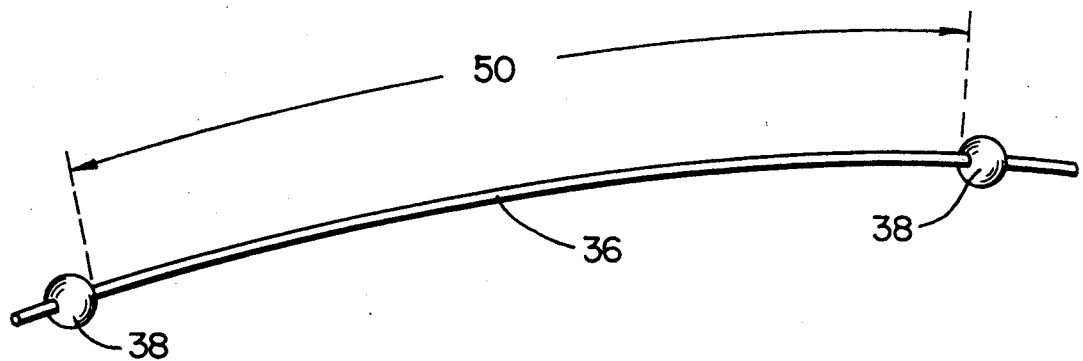
FIG. 8 is an enlarged perspective view of a segment of beaded dental floss that has been severed from a spool of beaded dental floss.
Figure 9:
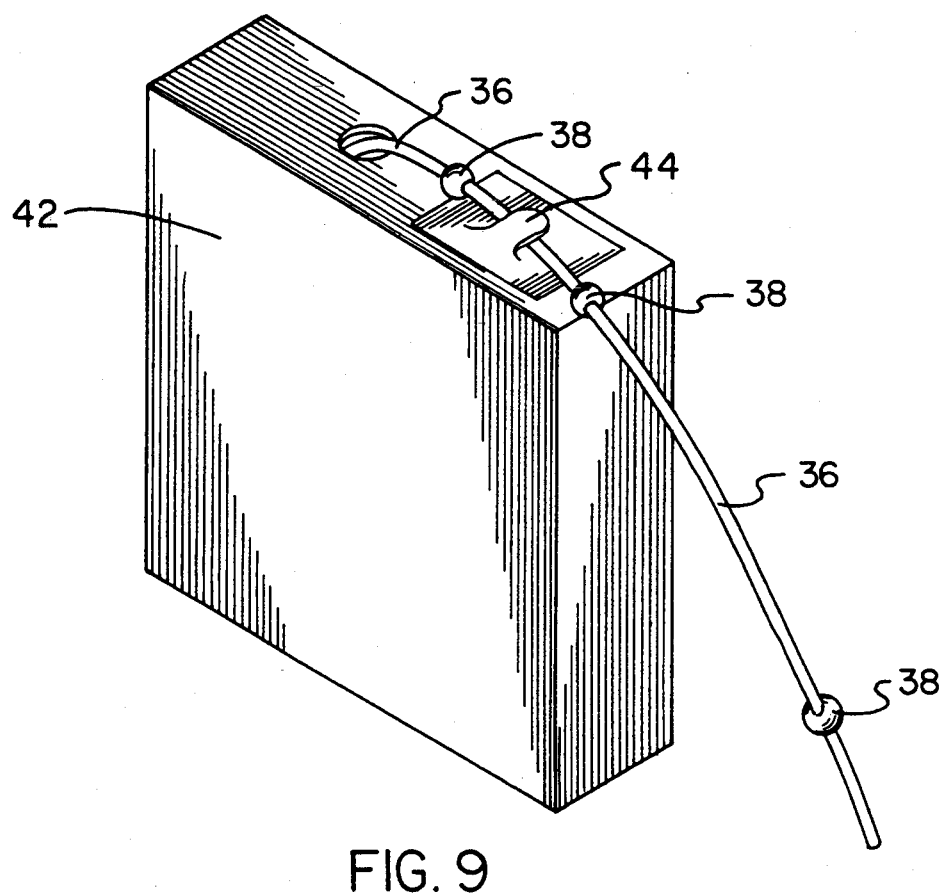
FIG. 9 is a perspective view of a dispenser for beaded dental floss on a spool such as used with the embodiment of the invention shown in FIG. 7.

In use, a segment of the beaded dental floss 36, shown in FIG. 8, is cut off of a spool of beaded dental floss 36 contained in a floss container 42. The beaded dental floss 36 is cut by blade 44 on the floss container 42. Once the beaded dental floss 36 is cut off of the spool, as shown in FIG. 8, one of the beads 38 is placed in one of the bead-receiving portions 48 of one of the dental floss receiving assemblies 13, and the other of the beads 38 is placed in another bead-receiving portion 48 of another dental floss receiving assembly 13. The distance 50 between beads 38 on the beaded dental floss 36 segment is selected so that when the beaded dental floss 36 segment is strung between opposing dental floss receiving assemblies 13 on opposing resilient finger assemblies 14, as shown in FIG. 6, the resilient finger assemblies 14 exert a prescribed tension on the beaded dental floss 36.

To install the beaded dental floss 36 on the resilient finger assemblies 14, the finger assemblies 14 may be slightly bent towards one another to temporarily decrease the transverse distance 40 between the finger assemblies 14. Once the beaded dental floss 36 is installed, the resilient finger assemblies 14 are released, and they exert tension on the beaded dental floss 36 held therebetween.

It is noted that the same hand-held dental floss applicator apparatus 10 of the invention can be used with either conventional dental floss, dental floss that is color coded as to where the floss should be cut and tied into a knot, and beaded dental floss.

The components of the hand-held dental floss applicator apparatus of the invention can be made from inexpensive and durable plastic and fibrous materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved hand-held dental floss applicator apparatus that is low in cost, relatively simple in design and operation, and which may advantageously be used without being wasteful of dental floss. With the invention, a hand-held dental floss applicator apparatus is provided which permits application of dental floss without placing a finger in the mouth. With the invention, a hand-held dental floss applicator apparatus is provided which does not include living hinges that are subject to plastic fatigue and breakage upon repeated use. With the invention, a hand-held dental floss applicator apparatus is provided which does not include a spool of dental floss carried in the hand-held device. With the invention, a hand-held dental floss applicator apparatus is provided which can use conventional dental floss provided on a spool. With the invention, a hand-held dental floss applicator apparatus is provided which is simple in design and construction, is simple in operation, and is inexpensive. With the invention, a hand-held dental floss applicator apparatus is provided which includes two taut segments of dental floss that are suitable for applying to the teeth and gums. With the invention, a hand-held dental floss applicator apparatus is provided which is provided with dental floss that has color markings which indicate places at which the dental floss should be cut off the spool to provide a dental floss segment for loading the hand-held dental flosser. With the invention, a hand-held dental floss applicator apparatus is provided which is provided with a spool of beaded dental floss that has beads spaced apart at predetermined distances to coincide with proper loading of the hand-held dental flosser.

With respect to the above description, it should be realized that the optimum dimensional relationships for the parts of the invention, to include variations in size, form function and manner of operation, assembly and use, are deemed readily apparent and obvious to those skilled in the art, and therefore, all relationships equivalent to those illustrated in the drawings and descried in the specification are intended to be encompassed only by the scope of appended claims.

While the present invention has been shown in the drawings and fully described above with particularity and detail in connection with what is presently deemed to be the most practical and preferred embodiments of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed as being new and desired to be protected by Letters Patent of the United States is as follows:

1. A hand-held dental floss applicator apparatus, comprising:
    a central body assembly,
    four finger assemblies rigidly attached to said central body assembly and projecting from said central body assembly, and
    four dental floss receiving assemblies connected to said respective four finger assemblies,
    wherein a centrally positioned longitudinal plane is perpendicular to a first plane and divides said central body assembly and said finger assemblies into two first bilaterally symmetrical portions, each of said first symmetrical portions lying on one side of said centrally positioned longitudinal plane, wherein a centrally positioned transverse plane is perpendicular to said first plane and divides said central body assembly and said finger assemblies into two second bilaterally symmetrical portions, each of said second symmetrical portions lying on one side of said centrally positioned transverse plane, wherein said central body assembly lies in said first plane, wherein a respective first portion of each of said respective finger assemblies projects from said central body assembly and is co-planar with said central body assembly, and wherein a respective second portion of each of said respective finger assemblies projects from each of said respective first portions of each of said respective finger assemblies and includes an end portion that lies in a second plane that is substantially perpendicular to said first plane and wherein at least one of said finger assemblies includes notch means for entraining dental floss therein.

2. The apparatus described in claim 1 wherein each of said respective dental floss receiving assemblies is formed as a notch in a respective finger assembly.

3. The apparatus described in claim 1 wherein each of said respective dental floss receiving assemblies includes a bead-receiving portion that has a shape complementary to a bead that it is capable of receiving.

4. The apparatus described in claim 1 wherein each of said respective dental floss receiving assemblies is formed as a notch in a respective end portion of said respective finger assemblies.

5. The apparatus described in claim 1 wherein said central body assembly includes two opposed dental floss receiving channels.

6. The apparatus described in claim 5 wherein said dental floss receiving channels are formed as indentations adjacent to flange portions formed in said central body assembly.

7. A combined hand-held dental floss applicator and dental floss apparatus, comprising:

a dental floss applicator which includes a central body assembly, four finger assemblies projecting from said central body assembly, and four dental floss receiving assemblies connected to said respective four finger assemblies, and a color coded dental floss which includes a spot of a first color which indicates where a segment of dental floss is to be cut and where a knot is to be formed and which includes a spot of a second color which indicates where the cut segment of dental floss is to be positioned with respect to a selected finger assembly when the segment of dental floss is threaded through the respective finger assemblies.

8. A combined hand-held dental floss applicator and dental floss apparatus, comprising:

a dental floss applicator which includes a central body assembly, four finger assemblies projecting from opposite ends of said central body assembly, and four dental floss receiving assemblies connected to said respective four finger assemblies wherein said dental floss receiving assemblies are adapted to receive respective beads of a beaded dental floss, and a beaded dental floss which includes beads spaced at predetermined intervals along a quantity of dental floss, said predetermined intervals corresponding to a transverse distance between opposite finger assemblies on opposite sides of a centrally positioned longitudinal plane that divides said central body assembly and said finger assemblies into two first bilaterally symmetrical portions, each of said first symmetrical portions lying on one side of said centrally positioned longitudinal plane.

* * * * *